United States Patent (10) Patent No.: US 9,333,549 B2
Fujii et al. (45) Date of Patent: May 10, 2016

(54) PRESS-FORMING MOLD DESIGNING METHOD AND PRESS-FORMING MOLD

(71) Applicant: JFE STEEL CORPORATION, Tokyo (JP)

(72) Inventors: Yusuke Fujii, Fukuyama (JP); Toyohisa Shinmiya, Fukuyama (JP); Yuji Yamasaki, Fukuyama (JP); Kazuhiko Higai, Chiba (JP)

(73) Assignee: JFE STEEL CORPORATION, Tokyo (JP)

( * ) Notice: Subject to any disclaimer, the term of this patent is extended or adjusted under 35 U.S.C. 154(b) by 0 days.

(21) Appl. No.: 14/368,062

(22) PCT Filed: Dec. 18, 2012

(86) PCT No.: PCT/JP2012/008062
§ 371 (c)(1),
(2) Date: Jun. 23, 2014

(87) PCT Pub. No.: WO2013/094177
PCT Pub. Date: Jun. 27, 2013

(65) Prior Publication Data
US 2015/0231682 A1 Aug. 20, 2015

(30) Foreign Application Priority Data
Dec. 21, 2011 (JP) ................. 2011-280464

(51) Int. Cl.
*B21D 22/02* (2006.01)
*B21D 37/20* (2006.01)
(Continued)

(52) U.S. Cl.
CPC ............... *B21D 22/02* (2013.01); *B21D 37/20* (2013.01); *B21J 13/02* (2013.01); *B30B 12/00* (2013.01); *B30B 15/02* (2013.01); *G01N 2203/0067* (2013.01)

(58) Field of Classification Search
CPC .......... B21D 22/02; B21D 5/00; B21D 37/20; G01N 3/06; G01N 2203/0064; G01N 2203/0066; G01N 2203/0067; G01N 2203/006; B21J 9/02; B21J 13/02; B30B 12/00; B30B 15/02; G06F 2217/41
See application file for complete search history.

(56) References Cited

U.S. PATENT DOCUMENTS 5,390,127 A * 2/1995 Tang et al. .................. 72/347
5,572,896 A * 11/1996 Story .......................... 72/350
(Continued)

FOREIGN PATENT DOCUMENTS

JP A-2001-79617 3/2001
JP A-2007-152407 6/2007
(Continued)

OTHER PUBLICATIONS
Mar. 19, 2013 International Search Report issued in International Application No. PCT/JP2012/008062.
(Continued)

*Primary Examiner* — Alexander P Taousakis
*Assistant Examiner* — Mohammad I Yusuf
(74) *Attorney, Agent, or Firm* — Oliff PLC

(57) ABSTRACT

A prediction equation "$R_0/t \geq (2R/t + (2R/t+1)\epsilon_f)/2(1-(1+2R/t)\epsilon_f)$" is derived which predicts that bendability-dominated fracture will not occur when the critical surface strain $\epsilon_{critical}$ is not exceeded by a strain on the metal sheet surface causing the occurrence of ductility-dominated fracture that is obtained from the minimum curvature radius $R_0$ of a press-forming mold and the critical strain $\epsilon_f$ in a plane strain region in a forming limit diagram. The minimum curvature radius $R_0$ of a mold required to prevent the occurrence of bendability-dominated fracture is estimated, and the mold is designed with a curvature radius that is not less than the curvature radius $R_0$.

8 Claims, 5 Drawing Sheets

(51) Int. Cl.
B30B 15/02 (2006.01)
B30B 12/00 (2006.01)
B21J 13/02 (2006.01)

(56) References Cited

U.S. PATENT DOCUMENTS 6,915,244 B2 * 7/2005 Yamano et al. .................. 703/2
8,584,496 B2 * 11/2013 Kuwayama et al. ........... 72/21.4

FOREIGN PATENT DOCUMENTS

JP  A-2009-255126  11/2009
JP  A-2010-69533  4/2010

OTHER PUBLICATIONS

Mar. 19, 2013 Written Opinion of the International Searching Authority issued in International Application No. PCT/JP2012/008062.
Gu et al., "Prediction of Forming Limit Diagram (FLD) and Effect of Work Hardening Property on FLD of Sheet Metals", *Tetsu-to-Haganè (Iron and Steel)*, 2002, pp. 38-44, vol. 88, No. 2 (with partial translation).
Apr. 29, 2015 Extended Search Report issued in European Patent Application No. 12858879.5.

* cited by examiner (a)

(b)

(a) SPECIMEN A (b) SPECIMEN B

PRESS-FORMING MOLD DESIGNING METHOD AND PRESS-FORMING MOLD

TECHNICAL FIELD

The present invention relates to a method for designing a press-forming mold such that a metal sheet can be press formed into a desired shape without the occurrence of fracture, and to a press-forming mold fabricated according to the method.

BACKGROUND ART

Press forming is one of the typical metal processing methods that produces a part with desired shape by the application of pressure to a metal sheet such as a steel sheet interposed between a pair of mold halves so that the metal sheet is formed in conformity with the shape of the mold. This technique is used in a wide range of fields such as manufacturing of automobile parts, machinery parts, building parts and home electric appliances.

In recent years, high strength steel sheets are increasingly used particularly in the press forming of automobile parts. However, workpieces having higher strength show lower press formability. This problem is addressed by improving both strength and elongation and thereby enhancing the mechanical properties of metal sheets themselves. A few of such metal sheets are dual phase steel sheets including hard and soft phases in the metal microstructure, and TRIP (transformation induced plasticity) steel sheets utilizing retained austenite. Such an approach is based on the fact that press formability is correlated to the elongation of metal sheets.

In general, the press formability of metal sheets is represented by a forming limit diagram. A forming limit diagram shows a critical value of strain at or immediately before the occurrence of fracture in metal sheets under the application of various types of biaxial stress to the metal sheets. In order to enhance the accuracy of the measurement or prediction of this forming limit, positive attempts have been made involving studies of the influences of various properties of materials (see, for example, Non Patent Literature 1).

Further, a technique has been developed which simulates press forming by a finite element method with use of a forming limit diagram to determine the forming conditions that will not cause fracture of metal sheets (see, for example, Patent Literature 1).

CITATION LIST

Non Patent Literature

[NPL 1] "Tetsu-to-Hagane (Iron and Steel)", Liwei Gu et al. (3 co-authors), The Iron and Steel Institute of Japan, Vol. 88 (2002), No. 2, pp. 88 to 94, "Prediction of Forming Limit Diagram (FLD) and Effect of Work Hardening Property on FLD of Sheet Metals"

Patent Literature

[PTL 1] Japanese Unexamined Patent Application Publication No. 2007-152407

SUMMARY OF INVENTION

Technical Problem

The present inventors performed press forming of high strength steel sheets under various forming conditions. As a result, the present inventors have found that the prediction of fracture based on the simulated press forming fails in many cases, and that fracture is caused by a mechanism different from that of ductility-dominated fracture illustrated in FIG. 1(a). After extensive studies, the present inventors have found that such fracture is strongly correlated with the bendability of metal sheets. That is, the fracture is a bendability-dominated fracture initiating from a crack on the sheet surface as illustrated in FIG. 1(b), and occurs even in the press forming of high strength steel sheets having excellent elongation. Accordingly, the conventional methods that evaluate press formability or predict the occurrence of fracture based on the ductility of metal sheets cannot predict the occurrence of bendability-dominated fracture. Thus, fracture may be caused even when metal sheets being press formed have excellent ductility.

The present invention has been made in order to solve the above problems. It is therefore an object of the invention to predict the shapes of molds required to prevent the occurrence of bendability-dominated fracture during press forming, and to design molds which can prevent the occurrence of bendability-dominated fracture.

Solution to Problem

To achieve the above object, the present inventors carried out extensive studies on the occurrence of bendability-dominated fracture. As a result, the present inventors have found that conditions causing the occurrence of bendability-dominated fracture are strongly correlated with the bendability R/t of metal sheets. Here, the bendability R/t is a mechanical property of metal sheets determined by a bending test as a ratio of the minimum bending radius R without the occurrence of a crack on the metal sheet surface (the minimum bending radius (the critical bending radius) with which a metal sheet can be bent without the occurrence of fracture), to the sheet thickness t. The present inventors have subjected various metal sheets to a 90-degree V-bending test and have found that bendability-dominated fracture is generated when a strain on the surface of a metal sheet being press formed exceeds the critical surface strain $\epsilon_{critical}$, which is the surface strain on the outwardly bent side that causes the occurrence of a crack on the surface of the metal sheet.

The present inventors have then invented the following prediction equation which predicts that bendability-dominated fracture will not occur when the critical surface strain $\epsilon_{critical}$ is not exceeded by a strain on the metal sheet surface causing the occurrence of ductility-dominated fracture that is obtained from the minimum curvature radius $R_0$ of a press-forming mold and the critical strain $\epsilon_f$ in a plane strain region in a forming limit diagram.

$$R_0/t \geq (2R/t + (2R/t+1)\epsilon_f)/2(1-(1+2R/t)\epsilon_f)$$

That is, the minimum curvature radius $R_0$ required for a mold to prevent the occurrence of bendability-dominated fracture is estimated based on the above equation, and the mold is designed with a curvature radius that is not less than the curvature radius $R_0$.

The present invention has been completed based on the above findings. A summary of the invention is as follows.

(1) A press-forming mold designing method wherein the minimum curvature radius $R_0$ of a press-forming mold is controlled to satisfy the following equation:

$$R_0/t \geq (2R/t + (2R/t+1)\epsilon_f)/2(1-(1+2R/t)\epsilon_f)$$

wherein $R_0$ is the minimum curvature radius of the press-forming mold, $\epsilon_f$ is the critical strain for the occurrence of fracture in a plane strain region of a metal sheet workpiece, t is the sheet thickness of the metal sheet workpiece, and R is the minimum bending radius allowing the metal sheet workpiece to be bent without the occurrence of fracture on the surface.

(2) The press-forming mold designing method described in (1), wherein the critical strain $\epsilon_f$ is obtained from a forming limit diagram of the metal sheet workpiece.

(3) A press-forming mold fabricated using the press-forming mold designing method described in (1) or (2).

Advantageous Effects of Invention

According to the present invention, bendability-dominated fracture may be prevented from occurring during press forming of metal sheet workpieces. Thus, the invention realizes stable press forming and significantly contributes to improving the press forming failure rate.

Further, the present invention allows for designing of a press-forming mold with accurate prediction of the shape with which the press-forming mold is to be fabricated, thus contributing to the reduction of the time required for manufacturing press-forming molds.

Furthermore, the present invention makes it possible to predict with high accuracy whether the metal sheets that have been selected are appropriate for press forming of various parts such as automobile panel parts and structural parts or frames.

DESCRIPTION OF EMBODIMENTS

Hereinbelow, embodiments of the present invention will be described with reference to the drawings.
(Preparation of Forming Limit Diagrams)

Figure 1:
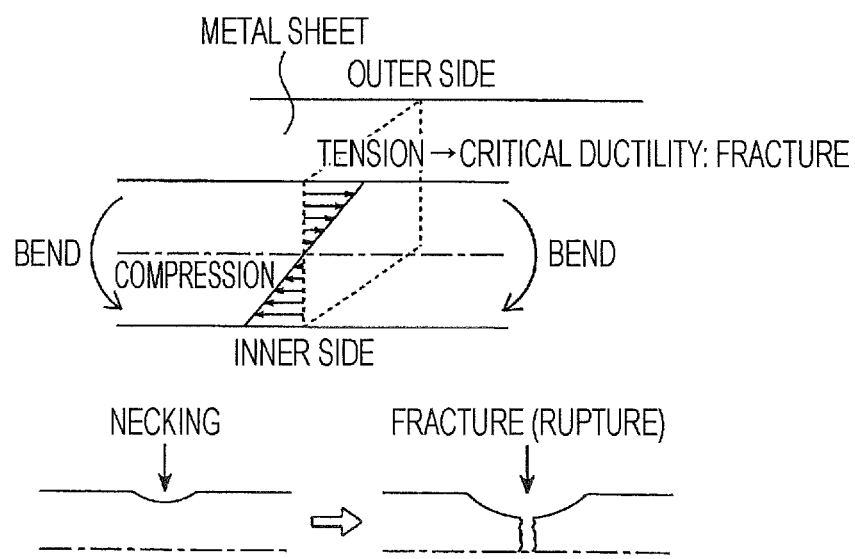
FIG. 1 is a set of views illustrating patterns of ductility-dominated fracture and bendability-dominated fracture in metal sheets.
Figure 1:
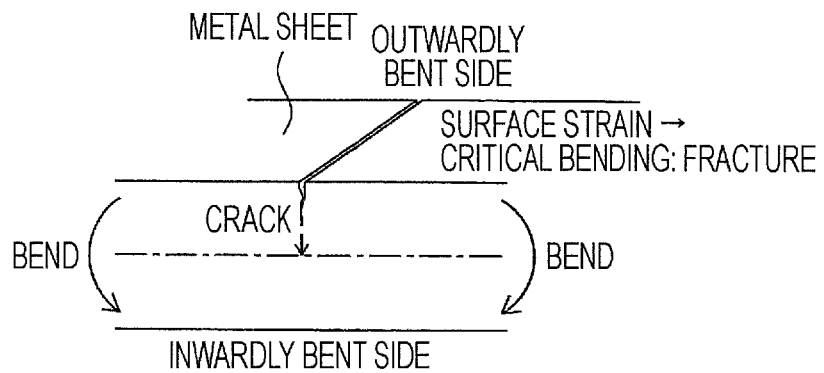
Figure 2:
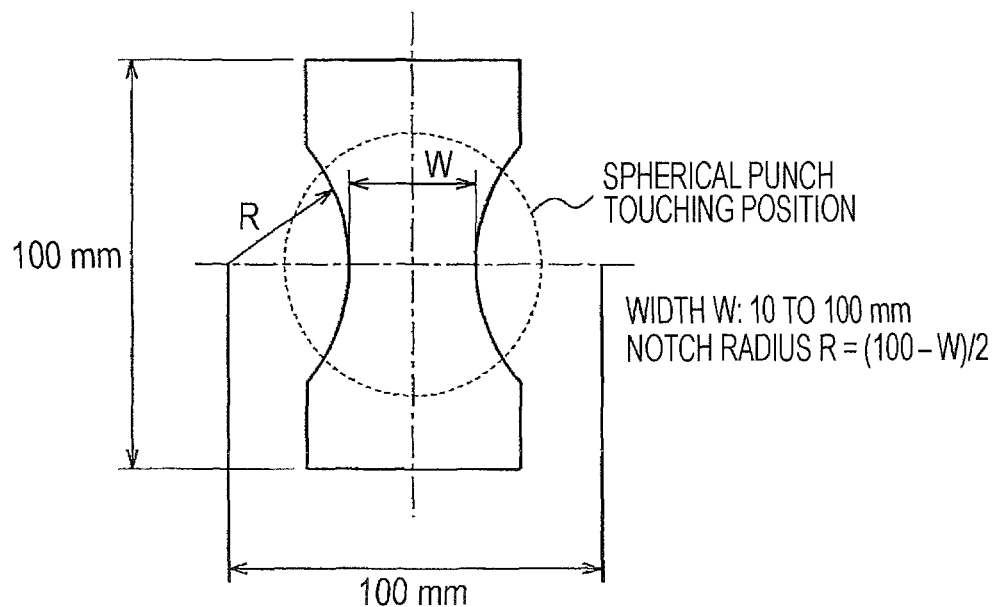
FIG. 2 is a view illustrating a shape of a test piece used in the preparation of a forming limit diagram.

To prepare a forming limit diagram (FLD), metal sheets are first processed into test pieces having various widths of 10 to 100 mm as illustrated in FIG. 2. Here, test pieces with various widths are provided in order to study the strain ratio (the ratio between minimum principal strain and maximum principal strain) over a wide range.

Next, marks are formed on the surface of the metal sheet. The marks may be of any shapes that allow strain to be measured after forming, with examples including circle patterns, dot patterns, grid patterns and concentric patterns. Any marking methods may be used such as electrolytic etching, photo etching and transferring of ink (stamp printing). However, scratching is not recommended because the occurrence of cracks is induced.

Next, the test piece is bulge formed with a spherical punch having a curvature radius of the tip of at least 25 mm. The bulging is terminated when fracture, necking or surface crack occurs in the sheet. The minimum curvature radius of the punch tip is limited to 25 mm because when the curvature radius falls below 25 mm, bending deformation comes to have a non-negligible influence at a region being deformed with the punch tip.

Figure 3:
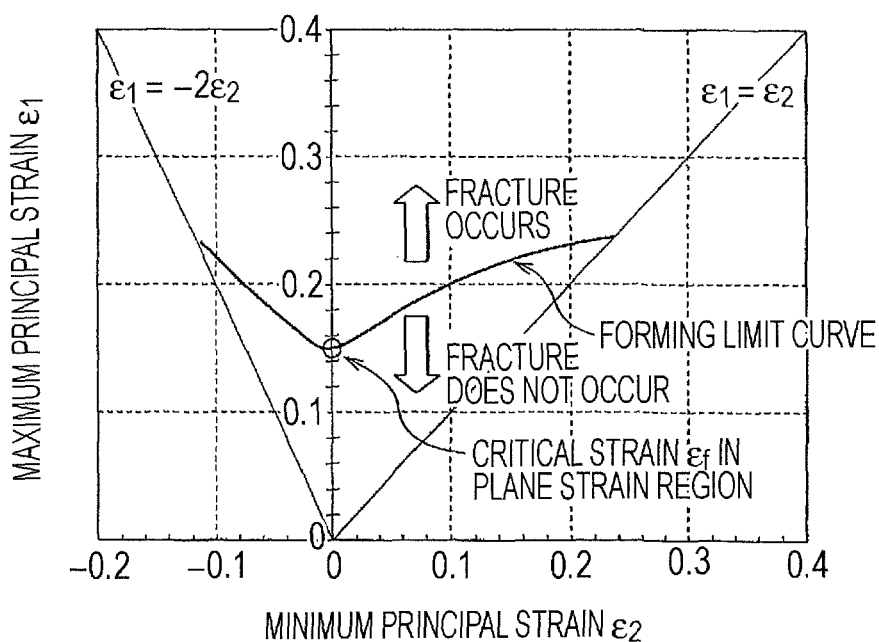
FIG. 3 is a view explaining a forming limit diagram.

After the termination of bulging, changes in the mark positions or the shape of the area touched by the punch tip are measured, thereby obtaining the maximum principal strain and the minimum principal strain. These procedures are repeated with respect to the test pieces having various widths to obtain the maximum principal strains and the minimum principal strains over a wide range. The results of the measurements of maximum principal strain and minimum principal strain are graphically described, thus providing a forming limit diagram such as one illustrated in FIG. 3. Here, a region where the minimum principal strain, such as in the case of bending deformation, is close to 0 is referred to as a plane strain region, and the critical strain in that region is represented by $\epsilon_f$ in FIG. 3.

In the conventional fracture prediction techniques relying on the ductility of metal sheets, the occurrence of fracture is predicted based on whether the strain is above or below the forming limit curve in the forming limit diagram, namely, whether the strain is in the fracture-occurring region or the fracture-free region. Fracture is predicted to occur when the strain is in the fracture-occurring region.
(Derivation of Prediction Equation)

An example will be discussed in which bendability required for metal sheets is predicted.

Based on the pure bending theory, the critical surface strain $\epsilon_{critical}$ on the outwardly bent side is represented by Equation (1) below:

$$\epsilon_{critical} = t/(t+2R) \quad (1)$$

wherein R is the critical bending radius of a metal sheet of interest in a 90-degree V-bending test, and t is the sheet thickness of the metal sheet.

Regarding a metal sheet which experiences bending deformation in a plane strain region during press forming, the critical strain $\epsilon_{R0}$ on the metal sheet surface is the sum of the critical strain $\epsilon_f$ in the plane strain region in the forming limit diagram plus additional strain due to bending deformation, as represented by Equation (2) below:

$$\epsilon_{R0} = \epsilon_f + t/(t+2R_0) \quad (2)$$

wherein $R_0$ is the minimum bending radius (minimum curvature radius) of a mold.

Since $\epsilon_{critical}$ is the critical strain prior to the occurrence of bendability-dominated fracture in a plane strain region, the requirement for the prevention of bending-induced fracture is represented by Equation (3):

$$\epsilon_{critical} \geq \epsilon_{R0} \quad (3)$$

Based on Equations (1) to (3), the minimum bending radius (minimum curvature radius) $R_0$ of a mold required to prevent the occurrence of bendability-dominated fracture may be obtained from Equation (4) below:

$$R_0/t \geq (2R/t + (2R/t+1)\epsilon_f)/2(1-(1+2R/t)\epsilon_f) \quad (4).$$

Accordingly, the occurrence of bendability-dominated fracture during press forming may be prevented by designing a mold such that its minimum bending radius (minimum curvature radius) is not less than the minimum bending radius (minimum curvature radius) $R_0$ described in Equation (4).

The molds of interest in the present embodiment are those having a minimum bending radius (minimum curvature radius) $R_0$ of less than 25 mm. This is because bending deformation comes to have a lower influence when metal sheets are press formed with a mold having a minimum bending radius (minimum curvature radius) $R_0$ of 25 mm or more and consequently ductility will be the factor that dominates fracture.

Further, the present embodiment assumes metal sheets having a sheet thickness t of not less than 0.5 mm, a tensile strength of not less than 980 MPa and a critical bending radius R of not less than 1 mm. When the sheet thickness t is less than 0.5 mm, the application of bending deformation to the metal sheets produces only a small surface strain on the outwardly bent side. Consequently, bendability-dominated fracture will not occur. Further, metal materials with a tensile strength of less than 980 MPa generally have excellent bendability. Furthermore, metal materials having a critical bending radius R of less than 1 mm are so excellent in bendability R/t that the minimum bending radius (minimum curvature radius) of molds generally used in press forming does not cause a problem of bendability-dominated fracture.

EXAMPLES

First, two specimens A and B shown in Table 1 which had substantially equal ductility (total elongation) and different levels of bendability were processed into several kinds of test pieces having a shape illustrated in FIG. 2 and a smallest width of 10 to 100 mm. The surface of the test pieces was subjected to electrolytic etching to form a dot pattern with dot intervals of 1.0 mm. Next, the test pieces were bulge formed with a spherical punch having a minimum curvature radius of the tip of 25 mm. The bulging with the spherical punch was continued until a fracture penetrated the steel sheet. With respect to the bulge formed test pieces, changes in dot intervals that had occurred in the vicinity of the punch tip were measured. The maximum principal strains and the minimum principal strains were thus determined, and a forming limit diagram was prepared.

TABLE 1

| Specimen | Sheet thickness t (mm) | Yield stress YS (MPa) | Tensile strength TS (MPa) | Total elongation El (%) | Critical bending radius R* (mm) | Bendability R/t |
|---|---|---|---|---|---|---|
| A | 1.62 | 860 | 1085 | 14.5 | 1.5 | 0.93 |
| B | 1.64 | 740 | 1180 | 15.0 | 3.5 | 2.13 |

*90-degree V-bending test

Figure 4:
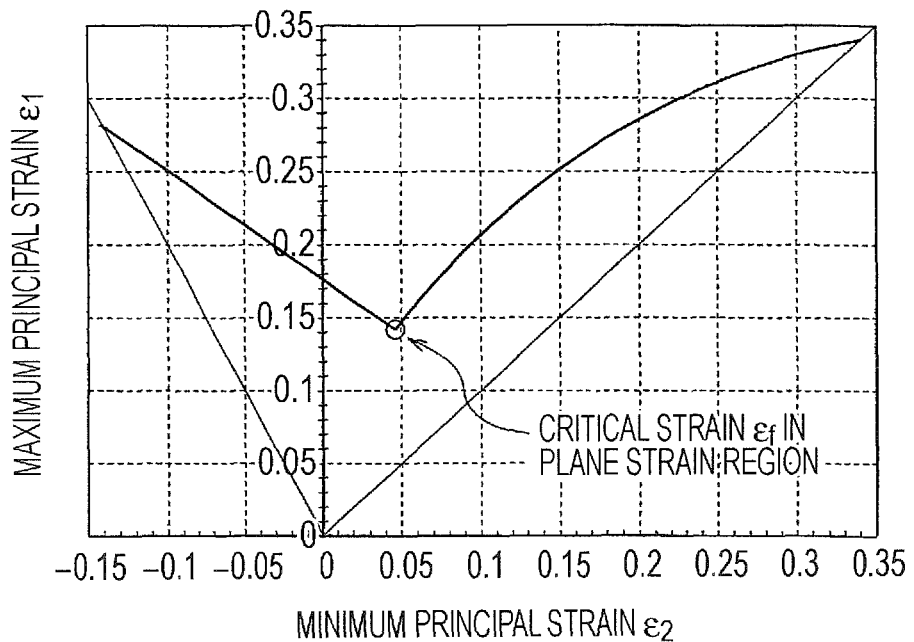
FIG. 4 is a set of views illustrating forming limit diagrams of specimen A and specimen B.
Figure 4:
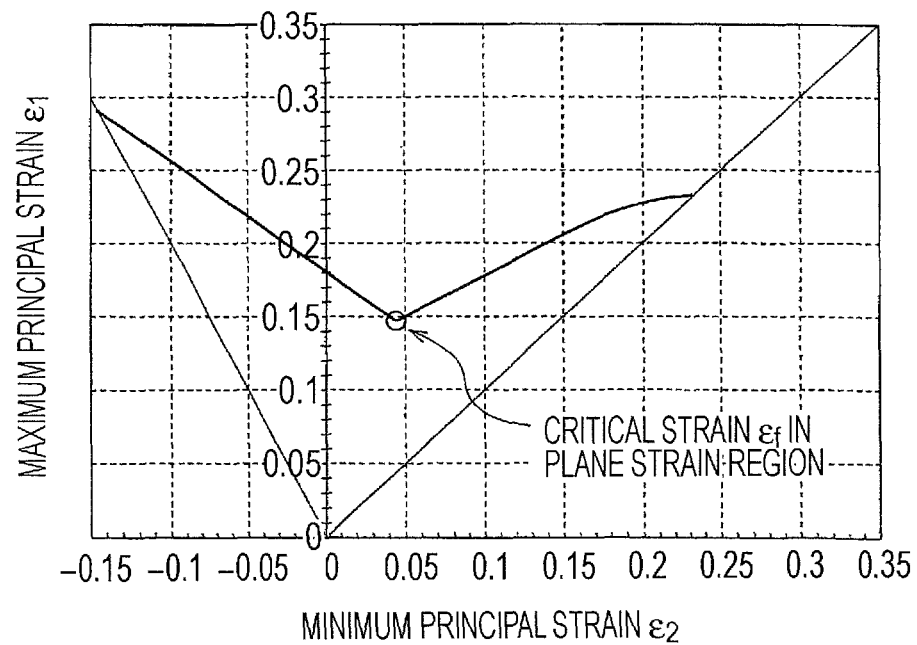

The forming limit diagrams of the specimens A and B prepared as described above are illustrated in FIGS. 4(a) and 4(b), respectively. Theoretically, a plane strain region is a region where the minimum principal strain is 0. In actuality, however, a plane strain region does not always agree with the axis where the minimum principal strain is 0 because of factors such as friction. In the measurement of critical bending radius R and bendability R/t of the specimens, the testing methods are not limited to the 90-degree V-bending test and other bending test methods such as U-bending test may be used. The critical strains $\epsilon_f$ in the plane strain region were obtained from the forming limit diagrams of the respective specimens, the results being described in Table 2.

TABLE 2

| Specimen | Critical strain $\epsilon_f$ in plane strain region |
|---|---|
| A | 0.14 |
| B | 0.15 |

Based on the critical strain $\epsilon_f$ and also the bendability R/t and the sheet thickness t of the metal sheet, the minimum bending radius (minimum curvature radius) $R_0$ required for a mold may be predicted from Equation (4). Table 3 describes the prediction of the minimum bending radius (minimum curvature radius) $R_0$ of a mold which can press form the specimen A or B without the occurrence of bendability-dominated fracture.

TABLE 3

| Specimen | A | B |
|---|---|---|
| Minimum bending radius $R_0$ required for mold | $R_0 \geq 3.05$ (mm) | $R_0 \geq 19.6$ (mm) |

(Verification of Example)

Figure 5:
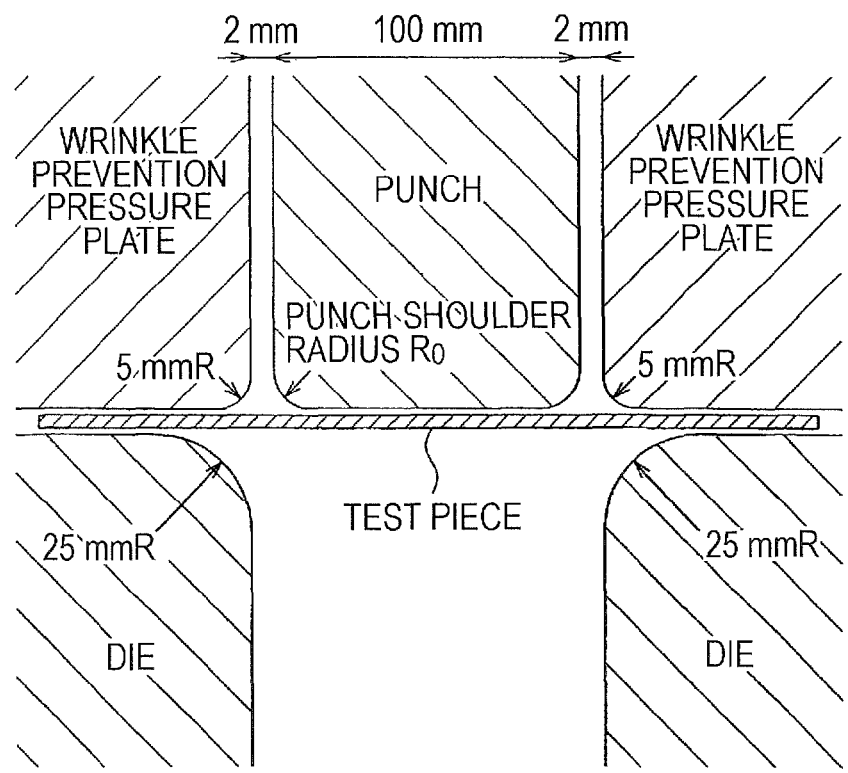
FIG. 5 is a view illustrating a shape of a hat mold.
Figure 6:
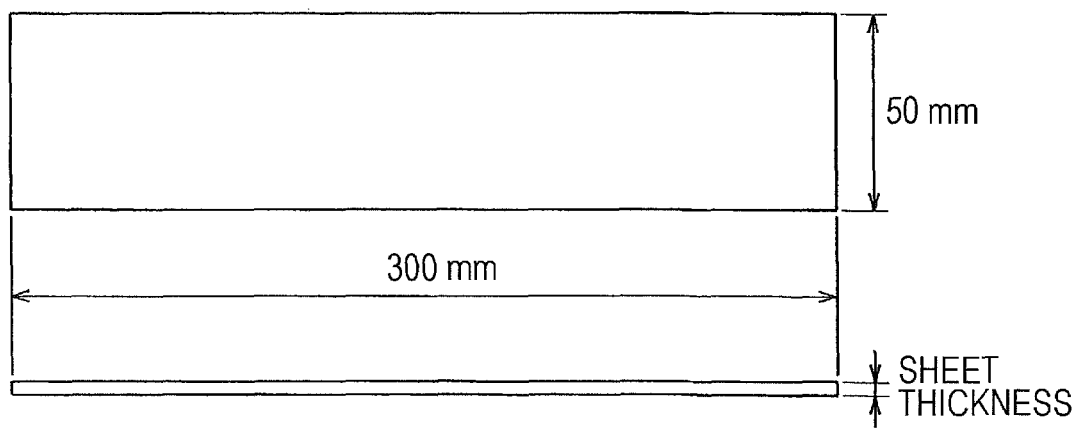
FIG. 6 is a view illustrating a shape of a test piece used in hat molding.

The above results of the prediction of the minimum bending radius (minimum curvature radius) $R_0$ required for a mold will be verified by forming flat sheet workpieces into a hat shape with a mold illustrating in FIG. 5. The workpieces are processed into rectangular specimens illustrated in FIG. 6, which are then formed with punches having various punch shoulder radiuses $R_0$. General antirust oil was used for lubrication. The wrinkle prevention pressure load was 15 tons. The hat height was 50 mm. The occurrence of bendability-dominated fracture in the specimens was checked.

The experiment results are described in Table 4, in which the symbol x shows the occurrence of bendability-dominated fracture and the symbol ○ indicates that forming was completed without the occurrence of bendability-dominated fracture. The specimen A was fractured during forming when the minimum bending radius (minimum curvature radius) $R_0$ of the mold was 3 mm or less. The specimen B was fractured during forming when the minimum bending radius (minimum curvature radius) $R_0$ of the mold was 19 mm or less.

TABLE 4

| | Minimum bending radius $R_0$ of mold (mm) | | | | | | | |
|---|---|---|---|---|---|---|---|---|
| Specimen | 2 | 3 | 4 | 5 | 18 | 19 | 20 | 21 |
| A | X | X | ○ | ○ | ○ | ○ | ○ | ○ |
| B | X | X | X | X | X | X | ○ | ○ |

Figure 7:
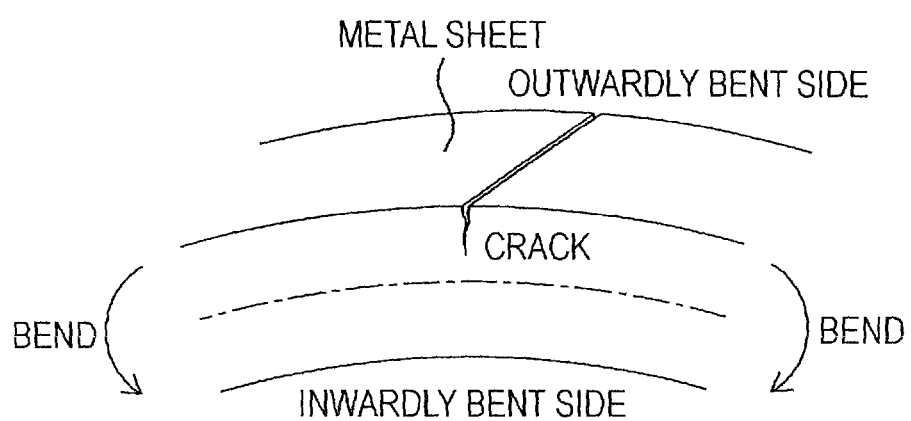
FIG. 7 is a schematic view illustrating a specimen subjected to hat molding to fracture.

With respect to the specimens formed to the occurrence of bendability-dominated fracture, a portion thereof subjected to forming in the vicinity of the punch shoulder is schematically illustrated in FIG. 7. A crack on the surface of each specimen indicates an initiation of bendability-dominated fracture. From these results, it has been demonstrated that molds which can prevent the occurrence of bendability-dominated fracture may be designed by determining the minimum bending radius (minimum curvature radius) $R_0$ of the molds based on the inventive prediction equation (4).

The scope of the invention is not limited to the embodiments described hereinabove. Although the above EXAMPLE illustrates the application of the invention to steel sheets having a tensile strength of not less than 980 MPa (1180 MPa grade steel sheets) and the present invention is suitably applied to the press forming of such high strength steel sheets, the invention may be applied to metal sheets other than steel sheets.

The invention claimed is:

1. A press-forming mold designing method comprising:
providing a metal sheet workpiece having a sheet thickness t;

determining a minimum curvature radius $R_0$ of a press-forming mold surface, the minimum curvature radius $R_0$ satisfying the following equation:

$$R_0/t \geq (2R/t+(2R/t+1)\epsilon_f)/2(1-(1+2R/t)\epsilon_f)$$

wherein:
$\epsilon_f$ is a critical strain for the occurrence of fracture in a plane strain region of an outwardly bent side of the metal sheet workpiece, and
R is a critical bending radius defined as a minimum bending radius allowing the metal sheet workpiece to be bent without the occurrence of fracture on an outwardly bent surface of the metal sheet workpiece; and
fabricating a press-forming mold having a punch, wherein a surface of the punch that is configured to contact the metal sheet workpiece does not have any portion with a radius of curvature less than the minimum curvature radius $R_0$.

2. The press-forming mold designing method according to claim 1, further comprising:

determining the critical strain $\epsilon_f$ from a forming limit diagram of the metal sheet workpiece.

3. A press-forming mold fabricated using the method described in claim 1.

4. A press-forming mold fabricated using the method described in claim 2.

5. The press-forming mold designing method according to claim 1, wherein the sheet thickness t is not less than 0.5 mm.

6. The press-forming mold designing method according to claim 1, wherein the critical bending radius R is not less than 1 mm.

7. The press-forming mold designing method according to claim 1, wherein a tensile strength of the metal sheet workpiece is not less than 980 MPa.

8. The press-forming mold designing method according to claim 1, wherein the sheet thickness t is not less than 0.5 mm, the critical bending radius R is not less than 1 mm, and a tensile strength of the metal sheet workpiece is not less than 980 MPa.

* * * * *